United States Patent [19]

Cipolli et al.

[11] Patent Number: 5,223,560
[45] Date of Patent: Jun. 29, 1993

[54] SELF-EXTINGUISHING POLYMERIC COMPOSITIONS

[75] Inventors: Roberto Cipolli, Seregno; Enrico Masarati, Castelnovo Valtidone; Gilberto Nucida, S. Giuliano Milanese; Mario Pirozzi, S. Donato Milanese; Roberto Oriani, Bergamo, all of Italy

[73] Assignee: Ministero Dell'Universita' E Della Ricerca Scientifica E Tecnologica, Rome, Italy

[21] Appl. No.: 917,533

[22] Filed: Jul. 21, 1992

Related U.S. Application Data

[63] Continuation of Ser. No. 572,601, Aug. 27, 1990, abandoned.

[30] Foreign Application Priority Data

Aug. 28, 1989 [IT] Italy ............... 21562 A/89
Mar. 27, 1990 [IT] Italy ............... 19839 A/90

[51] Int. Cl.$^5$ .................. C08K 5/3492; C08K 3/32
[52] U.S. Cl. ........................... 524/100; 529/416
[58] Field of Search ................. 524/100, 416

[56] References Cited

U.S. PATENT DOCUMENTS

| | | | |
|---|---|---|---|
| 4,263,434 | 4/1981 | Cassandrini et al. | 524/100 |
| 4,314,933 | 2/1982 | Berner | 524/100 |
| 4,333,869 | 6/1982 | Marciandi et al. | 524/416 |
| 4,504,610 | 3/1985 | Fontanelli et al. | 524/416 |
| 4,727,102 | 2/1988 | Scarso | 524/416 |
| 4,812,499 | 3/1989 | Cipriani et al. | 524/416 |
| 5,019,613 | 5/1991 | Ravichandran et al. | 524/100 |
| 5,045,577 | 9/1991 | Mullhaupt et al. | 524/100 |

*Primary Examiner*—Kriellion S. Morgan
*Attorney, Agent, or Firm*—Stevens, Davis, Miller & Mosher

[57] ABSTRACT

Polymeric compositions endowed with high self-extinguishing characteristics when exposed to a flame, based on thermoplastic polymers or polymers endowed with elastomeric properties, in particular olefinic polymers or copolymers comprising:

(a) from 89 to 45 parts by weight of a thermoplastic polymer, or of a polymer, or of a polymer endowed with elastomeric properties;

(b) from 8 to 30 parts by weight of one or more ammonium or amine phosphate(s) and/or phosphonate(s);

(c) from 3 to 25 parts by weight of one or more compound(s) derivatives of 2,4,6-triamino-1,3,5-triazine, having the general formula (I):

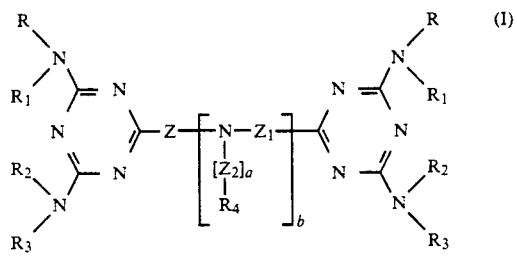

12 Claims, No Drawings

SELF-EXTINGUISHING POLYMERIC COMPOSITIONS

This application is a continuation of application Ser. No. 07/572,601, filed Aug. 27, 1990 now abandoned.

FIELD OF THE INVENTION

The present invention relates to self-extinguishing compositions based on thermoplastic polymers or on polymers endowed with elastomeric properties, in particular olefinic polymers or copolymers, containing special triazinic compounds in combination with ammonium or amine phosphates and/or phosphonates.

BACKGROUND OF THE INVENTION

Several solutions are known in the art in order to reduce or eliminate the combustibility of polymers. Some of such solutions are based on the use of metal compounds, in particular of antimony, bismuth or arsenic, in combination with partially halogenated, thermally unstable organic compounds, such as chlorinated paraffinic waxes.

Other solutions are based on the use of substances capable of yielding intumescence. The formulations of intumescent type are constituted by the polymer and at least three main additives: an essentially phosphorous-containing additive, whose purpose is of forming, during the combustion, an impermeable, semi-solid vitreous layer, essentially constituted by polyphosphoric acid, and of activating the process of formation of intumescence; a second additive, containing nitrogen, which performs the functions of a foaming agent; and a third, carbon-containing additive, which acts as a carbon donor for the formation of an insulating cellular carbonaceous layer ("char") between the polymer and the flame.

Examples of intumescent formulations of this type are those reported by the following patents: U.S. Pat. No. 3,810,862 (Phillips Petroleum Co.) based on melamine, pentaerythritol and ammonium polyphosphate; U.S. Pat. No. 4,727,102 (Vamp S.r.l.), based on melamine cyanurate, a hydroxyalkyl derivative of isocyanuric acid and ammonium polyphosphate; and by published patent application WO-85/05626 (Plascoat U.K. Limited), on the basis of various phosphorous and nitrogen compounds among which, in particular, a combination of melamine phosphate, pentaerythritol and ammonium polyphosphate.

In more recent formulations, together with the use of an organic or inorganic phosphorus compound a nitrogen-containing organic compound was used, generally consisting of an aminoplastic resin obtained by means of condensation of urea, melamine or dicyandiamide with formaldehyde.

Examples of formulations containing two additives are those reported in the following patents: U.S. Pat. No. 4,504,610 (Montedison S.p.A.) based on oligomeric derivatives of 1,3,5-triazine and ammonium polyphosphate and European patent 14,463 (Montedison S.p.A.) based on organic compounds selected from among benzylguanamine and reaction products between aldehydes and several nitrogenous cyclic compounds, in particular benzylguanamine-formaldehyde copolymers, and ammonium polyphosphate.

Self-extinguishing compositions can be also obtained by using single-component additives, which contain in their organic molecule both nitrogen and phosphorus, as disclosed in U.S. Pat. No. 4,201,705 (Borg-Wagner Corp).

These intumescent flame retardant systems endow the polymer which contains them with the property of forming a carbonaceous residue when they undergo a fire, or are exposed to the application of a flame. The flame-retardant systems of this kind display a large number of advantages: absence of phenomena of corrosion in the machinery in which the polymers are processed, a lower emission of smokes as compared to the systems containing metal compounds and halogenated hydrocarbons, and above all, the possibility of endowing the polymers with satisfactory flame-proof properties, with a smaller amount of total additive and therefore without excessively impairing the mechanical properties of the same polymers.

Applicants have found now that polymeric compositions endowed with extremely good flame-proof properties are obtained when a category of compounds derivative of 2,4,6-triamino-1,3,5-triazine are used, the effectiveness of which results to be even greater than of the products known from the prior art.

DESCRIPTION OF THE INVENTION

More specifically, the compositions according to the present invention comprise:

(a) from 89 to 45 parts by weight of a thermoplastic polymer, or of a polymer endowed with elastomeric properties;

(b) from 8 to 30 parts, and preferably from 12 to 30 parts by weight of one or more ammonium or amine phosphate(s) and/or phosphonate(s);

(c) from 3 to 25 parts, and preferably from 6 to 20 parts by weight of one or more compound(s) derivatives of 2,4,6-triamino-1,3,5-triazine, having the general formula (I):

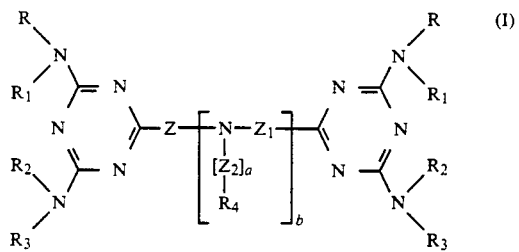

wherein the radicals from R to $R_3$, which can be either equal to or different from one another, and can have different meanings in each triazinic ring, are: H; ($C_1$–$C_{18}$)-alkyl; ($C_2$–$C_8$)-alkenyl; ($C_6$–$C_{16}$)-cycloalkyl or -alkylcycloalkyl, possibly substituted with a hydroxy or ($C_1$–$C_4$)-hydroxyalkyl function; —[—$C_nH_{2n}$—]—O—$R_5$;

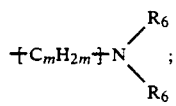

wherein:

n = an integer comprised within the range of from 2 to 8, preferably from 2 to 4;

m = an integer comprised within the range of from 2 to 6; $R_5$ = H; ($C_1$–$C_8$)-alkyl, preferably H or ($C_1$–$C_4$)-alkyl; ($C_2$–$C_6$)-alkenyl; —[—$C_pH_{2p}$—]—O—$R_7$, wherein p is an integer comprised within the range of from 1 to 4 and $R_7$ is either H or a $(C_1-C_4)$-alkyl; $(C_6-C_{12})$-cycloalkyl or -alkylcycloalkyl;

the radicals $R_6$, which can be either equal to or different from one another, are:

H; $(C_1-C_8)$-alkyl; $(C_2-C_6)$-alkenyl; $(C_6-C_{12})$-cycloalkyl or -alkylcycloalkyl; $(C_1-C_4)$-hydroxyalkyl; or the moiety:

is replaced by a heterocyclic radical linked to the alkyl chain through the nitrogen atom and possibly containing another heteroatom preferably selected from the group consisting of O, N, S;

or in general formula (I) at least one of the moieties

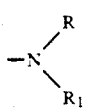

and

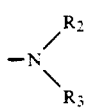

is replaced by a heterocyclic radical liked to the triazinic ring through the nitrogen atom and possibly containing another heteroatom preferably selected from the group consisting of O, N, S;

a is either 0 or 1;

b is 0 or an integer comprised within the range of from 1 to 5;

$R_4$ is hydrogen or;

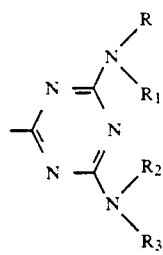

and its meaning can vary inside each repeating unit; when b is zero.

Z is a divalent radical comprised in one of the following formulas:

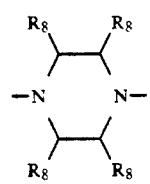
(II)

where radicals $R_8$, like or different from one another, are hydrogen or $(C_1-C_4)$alkyl;

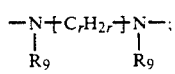
(III)

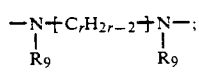
(IV)

where r is an integer comprised within the range of from 2 to 14; $R_9$ is hydrogen; $(C_1-C_4)$-alkyl; $(C_2-C_6)$-alkenyl; $(C_1-C_4)$-hydroxyalkyl;

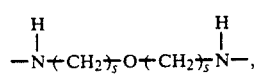
(V)

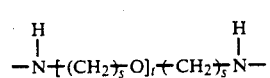
(VI)

where s is an integer comprised within the range of from 2 to 5 and t is an integer comprised within the range of from 1 to 3;

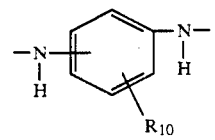
(VII)

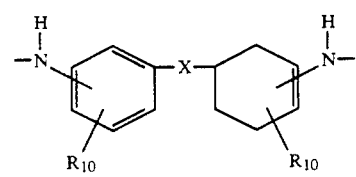
(VIII)

where:
X is a direct bond C—C; O; S; S—S; SO; SO$_2$; NH; NHSO$_2$; NHCO; N=N; CH$_2$;
$R_{10}$ is hydrogen; hydroxyl; $(C_1-C_4)$-alkyl; $(C_1-C_4)$-alkoxy;

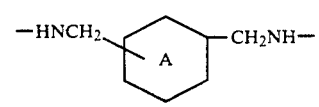
(IX)

where A can be a saturated or unsaturated cycle;

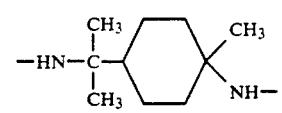
(X)

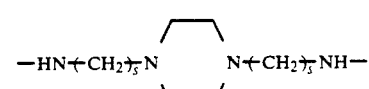
(XI)

where s has the hereinabove defined meaning;

when b is an integer comprised within the range of from 1 to 5, the group;

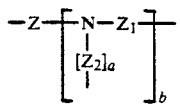

is a polyvalent radical comprised in one of the following formulas:

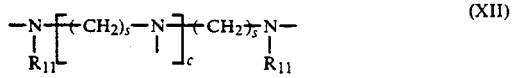 (XII)

where:
$R_{11}$ is either hydrogen or $(C_1-C_4)$-alkyl;
c is an integer comprised within the range of from 1 to 5; the indexes s, which can be either equal to or different from each other, have the hereinabove defined meaning;

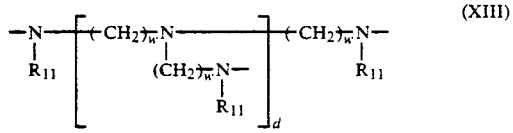 (XIII)

where:
$R_{11}$ has the hereinabove defined meaning;
w is an integer comprised within the range of from 2 to 4;
d is either 1 or 2.

Belonging to compounds of general formula (I) also are those derivatives having asymmetrical structure in that the radicals from R to $R_3$ can have different meanings in each triazinic ring.

The above said compounds of general formula (I), besides having a simple structure based on polycondensates of 2,4,6-triamine-1,3,5-triazine, are particularly stable when heated and therefore retain a high activity as flame retardants also after the hot-fabrication processes of the polymeric compositions which contain them.

The compositions according to the present invention are furthermore endowed with the advantage that in case of a fire they give rise to a very moderate and not obscuring smoke emission.

Examples of radicals from R to $R_3$ in the above general formula (I) are:

methyl; ethyl; propyl; isopropyl; n-butyl; isobutyl; tert-butyl; n-pentyl; isopentyl; n-hexyl; tert-hexyl; octyl; tert-octyl; decyl; dodecyl; octadecyl; ethenyl; propenyl; butenyl; isobutenyl; hexenyl; octentyl; cyclohexyl; propylcyclohexyl; butylcyclohexyl; decyclohexyl; idroxycyclohexyl; idroxyethylcyclohexyl; 2-hydroxyethyl; 2-hydroxypropyl; 3-hydroxypropyl; 3-hydroxybutyl; 4-hydroxybutyl; 3-hydroxypentyl; 5-hydroxypentyl; 6-hydroxyhexyl; 3-hydroxy-2,5-dimethylhexyl; 7-hydroxyheptyl; 7-hydroxyoctyl; 2-methoxyethyl; 2-methoxypropyl; 3-methoxypropyl; 4-methoxybutyl; 6-methoxyhexyl; 7-methoxyheptyl; 7-methoxyoctyl; 2-ethoxyethyl; 3-ethoxypropyl; 4-ethoxybutyl; 3-propoxypropyl; 3-butoxypropyl; 4-butoxybutyl; 4-isobutoxybutyl; 5-propoxypentyl; 2-cyclohexyloxyethyl; 2-ethenyloxyethyl; 2-(N,N-dimethylamino)ethyl; 3-(N,N-dimethylamino)propyl; 4-(N,N-dimethylamino)butyl; 5-(N,N-dimethylamino)pentyl; 4-(N,N-diethylamino)butyl; 5-(N,N-diethylamino)pentyl; 5-(N,N-diisopropylamino)pentyl; 3-(N-ethylamino)propyl; 4-(N-methylamino)butyl; 4-(N,N-dipropylamino)butyl; 2-(N,N-diisopropylamino)ethyl; 6-(N-hexenylamino)hexyl; 2-(N-ethenylamino)ethyl; 2-(N-cyclohexylamino)ethyl; 2-(N-2-hydroxyethylamino)ethyl; 2-(2-hydroxyethoxy)ethyl; 2-(2-methoxyethoxy)ethyl; 6-(N-propylamino)hexyl; and so forth.

Examples of heterocyclic radicals which can replace the moieties:

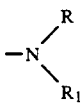

and

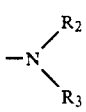

are:
aziridine; pyrrolidine; piperidine; morpholine; thiomorpholine; piperazine; 4-methylpiperazine; 4-ethylpiperazine; 2-methylpiperazine; 2,5-dimethylpiperazine; 2,3,5,6-tetramethylpiperazine; 2,2,5,5-tetramethylpiperazine; 2-ethylpiperazine; 2,5-diethylpiperazine; and so forth.

Examples of heterocyclic radicals which can replace the moiety:

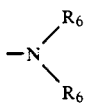

are:
aziridine; pyrrolidine; piperidine; morpholine; thiomorpholine; piperazine; 4-methylpiperazine; 4-ethylpiperazine; and so forth.

Examples of divalent -Z- radicals are the ones deriving by elimination of a hydrogen from each aminic group, from the following diaminic compounds: piperazine; 2-methylpiperazine; 2,5-dimethylpiperazine; 2,3,5,6-tetramethylpiperazine; 2-ethylpiperazine; 2,5-diethylpiperazine; 1,2-diaminoethane; 1,3-diaminopropane; 1,4-diaminobutane; 1,5-diaminopentane; 1,6-diaminohexane; 1,8-diaminooctane; 1,10-diaminodecane; 1,12-diaminododecane; N,N'-dimethyl-1,2-diaminoethane; N-methyl-1,3-diaminopropane; N-ethyl-1,2-diaminoethane; N-isopropyl-1,2-diaminoethane; N-(2-hydroxyethyl)-1,2-diaminoethane; N,N'-bis(2-hydroxyethyl)-1,2-diaminoethane; N-(2-hydroxyethyl)-1,3-diaminopropane; N-hexenyl-1,6-diaminohexane; N,N'-diethyl-1,4-diamino-2-butene; 2,5-diamino-3-hexene; 2-aminoethylether; (2-aminoethoxy)-methylether; 1,2-bis-(2-aminoethoxy)ethane; 1,3-diaminobenzene; 1,4-diaminobenzene; 2,4-diaminotoluene; 2,4-diaminoanisole; 2,4-diaminophenol; 4-aminophenylether; 4,4'-methylenedianiline; 4,4'-diaminobenzanilide; 3-aminophenylsulfone; 4-aminophenylsulfone; 4-aminophenyldisulfide; 4-aminophenylsulfoxide; 1,3-bis-(aminomethyl)benzene; 1,4-bis(aminomethyl)benzene; 1,3-bis(aminomethyl)cyclohexane; 1,8-diamino-p-methane; 1,4-bis(2-aminoethyl)piperazine; 1,4-bis(3- aminopropyl)piperazine; 1,4-bis(4-aminobutyl)piperazine; 1,4-bis(5-aminopentyl)piperazine; and so forth.

Examples of polyvalent radicals:

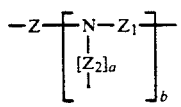

are those which derive, by elimination of a hydrogen atom from each reacted amino group, from the following polyaminic compounds: bis(2-aminoethyl)amine; bis(3-aminopropyl)amine; bis(4-aminobutyl)amine; bis(5-aminopentyl)amine; bis[2-N-methylamino)ethyl]amine; 2-N-butyl-bis(2-aminoethyl)amine; bis[3-(N-methylamino)propyl]amine; N-(3-aminopropyl)-1,4-diaminobutane; N-(3-aminopropyl)-1,5-diaminopentane; N-(4-aminobutyl)-1,5-diaminopentane; tris(2-aminoethyl)amine; tris(3-aminopropyl)amine; tris(4-aminobutyl)amine; tris[2-(N-ethylamino)ethyl]amine; N,N'-bis(2-aminoethyl)-1,2-diaminoethane; N,N'-bis(3-aminopropyl)-1,3-diaminopropane; N,N'-bis(2-aminoethyl)-1,3-diaminoethane; N,N'-bis(3-aminopropyl)-1,2-diaminoethane; N,N'-bis(3-aminopropyl-1,4-diaminobutane; bis[2-(2-aminoethyl)aminoethyl)amine; N,N'-bis[2-(2-aminoethyl)aminoethyl]1,2-diaminoethane; N,N'-bis[3-(2-aminoethyl)aminopropyl]-1,2-diaminoethane; N,N,N',N'-tetrakis(2-aminoethyl)-1,2-diaminoethane; and so forth.

The compounds of formula (I) in which at least one of the moieties:

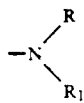

and

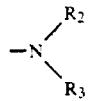

is replaced by one -NH$_2$ radical are preferred.

Specific compounds comprised within the scope of general formula (I) which can be advantageously used in the compositions according to the present invention are reported in the examples which follow the disclosure.

The compounds of general formula (I) can be prepared by reacting, at temperatures comprised within the range of from 0° to 10° C., and at a pH value comprised within the range of from 5 to 7, a halide of cyanuric acid, such as, e.g., cyanuric chloride, in a suitable solvent (such as, e.g., acetone, water, methylene chloride, and so forth) with an amine having the general formula (XIV):

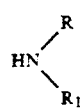

wherein R and R$_1$ have the hereinabove defined meaning, in the presence or less (according to the molar ratio used in the reaction) of an acid acceptor, such as, e.g., NaOH, NaHCO$_3$, Na$_2$CO$_3$ or triethylamine with the intermediate (XV):

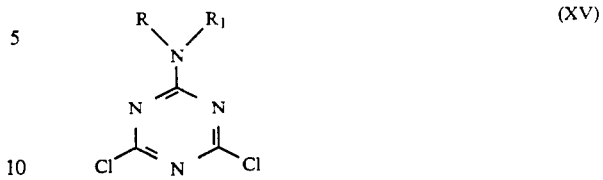

being obtained.

Such an intermediate, either separated or not separated from the reaction mixture, is subsequently reacted under conditions similar to those as hereinabove specified, but operating at a temperature comprised within the range of from 10° to 50° C. with an amine of general formula (XVI):

wherein R$_2$ and R$_3$ have the hereinabove defined meaning, with the intermediate (XVII):

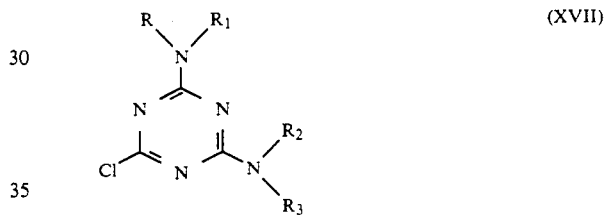

being obtained.

The intermediate (XVII) either separated or not, and in a number of moles smaller than, or equal to, (2+b), is reacted again under the same conditions as of the two first reaction steps, but operating at temperatures comprised within the range of from 70° to 150° C. and hence with solvents which also are compatible with such temperature values (such as, e.g., water, toluene, xylene, dimethylformamide, and so forth), with one mole of a polyamine having the general formula (XVIII):

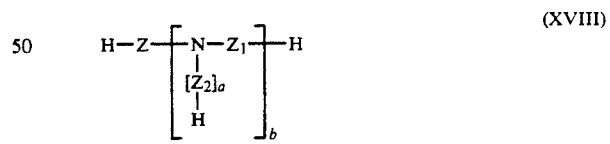

corresponding to one, of structures comprised within the range of general formulas form (II) to (XIII), with the compounds of general formula (I) being obtained as the end products.

In case compounds of general formula (I) containing equal moieties

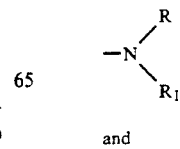

and

-continued $$-N\begin{matrix} R_2 \\ \diagdown \\ R_3 \end{matrix}$$

are desired, the process is carried out by reacting cyanuric chloride with two moles of an amine of general formula (XIV) under the same conditions as disclosed hereinabove in order to obtain the intermediate of general formula (XVII).

An alternative method consists of reacting a number of moles lower than, or equal to, (2+b) of a halide, such as, e.g., the chloride, or cyanuric acid with one mole of a polyamine of general formula (XVIII) as above defined, still under the same conditions as hereinabove disclosed, at a temperature comprised within the range of from 0° to 10° C. in order to yield the intermediate of general formula (XIX):

$$\text{(XIX)}$$

[Structure XIX showing two chlorinated triazine rings connected by -Z-[N-Z_1-[Z_2]_a-R_{12}]_b- linker]

wherein $R_{12}$ is hydrogen or:

[Structure of dichlorotriazinyl group]

and its meaning can vary inside each repeating unit.

Such an intermediate, either separated or not, is reacted once again:

(a) with a number of moles lower than, or equal to, (2+b) of an amine of general formula (XIV), at a temperature comprised within the range of from 40° to 80° C. in order to yield the intermediate of general formula (XX):

$$\text{(XX)}$$

[Structure XX showing two triazine rings with R, R_1 amine substituents connected by -Z-[N-Z_1-[Z_2]_a-R_{13}]_b- linker]

wherein $R_{13}$ hydrogen or:

[Structure of chlorotriazinyl group with NR_1R substituent]

and its meaning can vary inside each repeating unit; which intermediate, once again either separated or not, is reacted with a number of moles lower than, or equal to, (2+b) of an amine of general formula (XVI), at a temperature comprised within the range of from 80° to 150° C. and under similar conditions as those disclosed hereinabove; or (b) with a number of moles lower than, or equal to, 2(2+b) of an amine of general formula (XIV), at a temperature comprised within the range of from 80° to 150° C., under similar conditions as disclosed hereinabove.

Among the phosphates, ammonium polyphosphates falling within the scope of the general formula $$(NH_4)_{n+2}P_nO_{3n+1}$$

wherein n is an integer equal to, or greater than 2, are preferred; the molecular weight of polyphosphates should be high enough, to secure a low solubility in water. For indicative purposes, n is preferably comprised within the range of from 2 to 500.

The composition of the polyphosphates having the hereinabove indicated formula, in which n is a high enough numeral, and is preferably comprised within the range of from 5 to 500, practically is the one which corresponds to metaphosphate formula $$(NH_4PO_3)_n$$

An example of such polyphosphates is the product known under the trade name "Exolit 422" (manufactured and traded by Hoechst) and having the composition (NH$_4$PO$_3$)n in which n is greater than 50; another example is the product known under the mark "Phos-Chek P/30" (Monsanto Chemical), and having a similar composition.

Another polyphosphate which can be advantageously used, above all thanks to its low water solubility, is the product known under the trade name "Exolit 462" (manufactured and traded by Hoechst) and corresponding to Exolit 422 microencapsulated in melamine-formaldehyde resin.

Other phosphates which can be used are those which derive from amines, such as, e.g., dimethylammonium phosphate or diethylammonium phosphate, ethylenediamine phosphate, melamine ortho or pyrophosphate.

Among the phosphonates, good results have been achieved by using mono or polyammonium phosphonates selected from among the salts derived from mono or polyphosphonic acids.

Examples of such acids are: ethane-1,1,2-triphosphonic acid; ethane-2-hydroxy-1,1,2-triphosphonic acid; propane-1,2,3-triphosphonic acid, methylphosphonic acid; ethylphosphonic acid; n-propylphosphonic acid; n-butylphosphonic acid; phenylphosphonic acid; ethane-1-amino-1,1-diphosphonic acid; ethane-1-hydroxy-1,1-diphosphonic acid; dodecane-1-hydroxy- 1,1-diphosphonic acid; phosphonoacetic acid; 2-phosphonopropionic acid; 3-phosphonopropionic acid; 2-phosphonobutyric acid; 4-phosphonobutyric acid, aminetri (methylenephosphonic) acid; ethylenediaminetetra (methylenephosphonic) acid; hexamethylenediaminetetra (methylenephosphonic) acid; diethylenetriaminepenta (methylenephosphonic) acid; and so forth.

Among the polymers which can be used in the compositions according to the present invention, preferred are polymers and copolymers of olefins of general formula $$R-CH=CH_2$$

wherein R is a hydrogen atom of a $(C_1-C_8)$-alkyl or -aryl radical, in particular:

(1) either isotactic or prevailingly isotactic polypropylene;
(2) HDPE, LLDPE, LDPE polyethylene;
(3) crystalline copolymers of propylene with minor proportions of ethylene and/or other alpha-olefins, such as 1-butene, 1-hexene, 1-octene, 4-methyl-1-pentene;
(4) heterophasic compositions comprising (A) a fraction constituted by a propylene homopolymer, or by one of the copolymers as per above item (3); and (B) a copolymeric fraction constituted by elastomeric copolymers of ethylene with an alpha-olefin, possibly containing minor proportions of a diene, wherein the alpha-olefin is preferably selected from among propylene and 1-butene;
(5) elastomeric copolymers of ethylene with alpha-olefins possibly containing minor proportions of a diene.

Examples of dienes more commonly contained in said elastomeric copolymers are butadiene, ethylydene-norbornene, hexadiene-1,4.

Among the polymers of olefins of general formula $R-CH=CH_2$ wherein R is an aryl radical, "crystal" and impact-resistant polystyrene are preferred.

Other examples of polymers which can be commonly used are acrylonitrile/butadiene/styrene copolymers (ABS); styrene/acrylonitrile copolymers (SAN); polyurethane (of either polyester or polyether grade); poly(ethyleneterephthalate); poly(butyleneterephthalate), polyamides and so forth.

The self-extinguishing compositions according to the present invention can be prepared according to methods known from the prior art, for example, ammonium or amine phosphate and/or phosphonate is first intimately mixed with one or more finely ground nitrogen-containing compounds of general formula (I) (the particles of which are generally smaller than 70 μm) and the so obtained mixture is added to the polymer in a turbomixer, to yield a homogenous mixture, which is either extruded or granulated. The so obtained granular product can be transformed into various finished articles according to any of the well-known molding techniques.

The fire-retardant additives according to the present invention are suited to be used also in the field of flame-retardant paints.

EXAMPLES

The following examples are given to illustrate but not to limit the characteristics of the invention.

EXAMPLE 1

73.8 g of cyanuric acid chloride, 240 g of acetone and 300 g of ice were charged into a 1 liter reactor equipped with stirrer, thermometer, dropping funnel, reflux cooler and cooling bath.

Under stirring and maintaining a temperature ranging from 0° to 5° C., 39.6 g of cyclohexylamine and 16.0 g of sodium hydrate dissolved in 40 g of water were simultaneously fed, in order to maintain a pH ranging from 5 to 7.

The whole was maintained at a temperature of 0°-5° C. for further 2 hours; then the obtained product was filtered and washed with water.

The cake was dried, so obtaining 87 parts of intermediate (XXI)

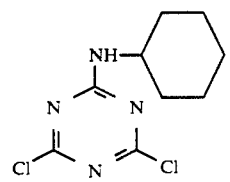

(XXI)

as a white crystalline powder having melting point (m.p.)=70°-71° C. and a chlorine content of 28.61% (theoretical value: 28.74%).

Into a 0.5 liter reactor equipped with stirrer, thermometer, feeding funnel, reflux cooler and heating bath, 74.1 g of intermediate (XXI) and 160 g of acetone were charged.

It was heated to 40° C. under stirring, until a solution was obtained, then 45 g of an ammonia solution at 30% by weight were added in 30 minutes, maintaining the temperature at 40° C.

It was then heated to 45° C., this temperature being maintained for 4 hours.

After cooling, the obtained product was filtered and then it was washed with water on the filter.

After drying in oven at 80° C., 67 g of intermediate (XXII):

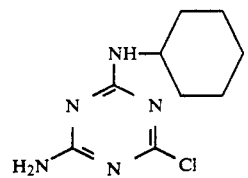

(XXII)

were obtained in the form of a white powder having m.p.=180°-183° C. and a chlorine content of 15.51% (theoretical value: 15.6%). The structure of compounds (XXI) and (XXII was confirmed by NMR analysis.

Into a 1 liter reactor equipped like the preceding reactor, 63.7 g of intermediate (XXII), 400 cm³ of xylene and 12.1 g of piperazine were charged.

Under stirring, the mixture was heated to 100° C., then in 4 hours and maintaining the temperature at 100° C., 11.2 g of sodium hydrate dissolved in 20 g of water were added. The temperature was gradually raised while azeotropically eliminating water, until reaching the solvent boiling temperature.

The whole was maintained under reflux for 12 hours, then the mass was cooled to room temperature, and the resulting product was filtered. The cake was thoroughly pressed and then repeatedly washed with water.

After drying, 62.5 g of product

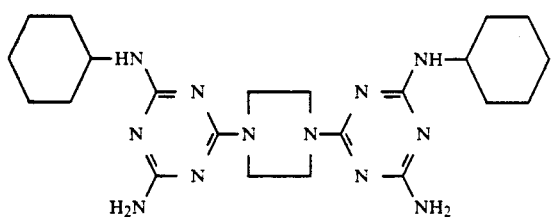

in the form of a white crystalline powder having m.p.=265°-268° C. were obtained.

EXAMPLE 2

Into a 3 liter reactor equipped with stirrer, thermometer, feeding funnel, reflux cooler and heating bath, 184.5 g of cyanuric acid chloride and 650 g of acetone were charged.

Under stirring, it was heated to 40° C. until a solution was obtained, then, in 1 hour and 30 minutes and maintaining the temperature at 40° C., 284 g of an ammonia solution at 30% by weight were added.

Then, it was heated to 45° C. and this temperature was maintained during 4 hours.

After cooling, the resulting product was filtered and washed with water on the filter.

After drying in oven at 50°-60° C. under vacuum, there were obtained 113 g of intermediate (XXIII):

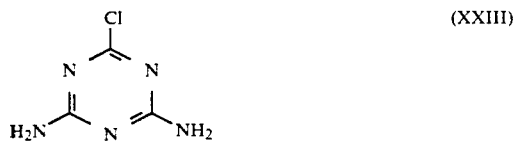

(XXIII)

in the form of a white crystalline, non-meltable powder having a chlorine content equal to 24.2% (theoretical: 24.4%).

The structure of this compound was also confirmed by infrared spectroscopic analysis.

Into a 1 liter reactor, equipped like the preceding one, 400 cm³ of xylene, 58.2 g of intermediate (XXIII) and 17.2 g of piperazine were charged.

The mass was heated to 100° C. and this temperature was maintained for 2 hours.

16 g of solid sodium hydrate were then charged and the whole was brought to boiling. It was refluxed for about 20 hours, then it was cooled to room temperature and filtered.

The cake was repeatedly washed with water and then dried.

54.2 g of product:

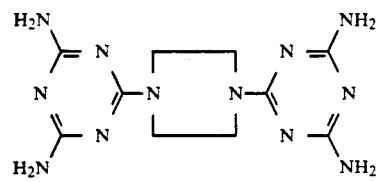

in the form of a white crystalline powder having m.p. higher than 300° C. were obtained.

EXAMPLE 3

Into the same 3 liter apparatus described in Example 2, but initially equipped with a cooling bath, 184.5 g of cyanuric acid chloride and 1,300 cm³ of methylene chloride were charged.

While cooling from the outside, 87.2 g of morpholine and 40 g of sodium hydrate dissolved in 150 g of water were simultaneously fed in 3 hours, maintaining pH value from 5 to 7 and a temperature from 0° to 3° C.

The temperature was maintained from 0° to 3° C. during further 3 hours, whereafter the aqueous phase was separated.

By distillation of methylene chloride, 230 g of intermediate (XXIV):

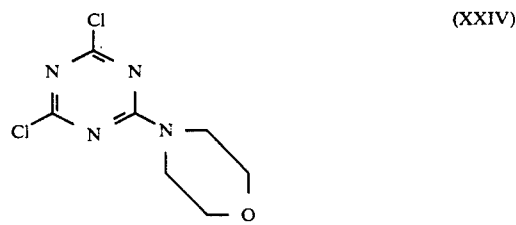

(XXIV)

in the form of a white crystalline powder, having m.p.=155°-157° C. and a chlorine content of 29.87% (theoretical value: 30.21%), were obtained.

Into a 0.5 liter reactor, equipped as described in Example 2, 200 g of a solution at 30% by weight of ammonia and 70.5 g of intermediate (XXIV) were charged.

It was heated to 50° C. and this temperature was maintained during 7 hours. The whole was allowed to cool to room temperature, the obtained product was filtered and washed with water.

The cake was dried, thereby obtaining 58 g of intermediate (XXV):

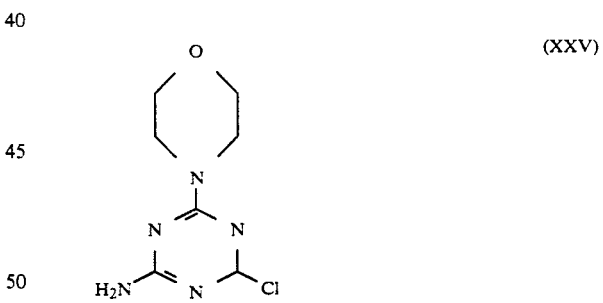

(XXV)

in the form of a white crystalline powder having m.p.=189°-191° C. and a chlorine content of 16.28% (theoretical value: 16.47%).

The structure of compounds (XXIV) and (XXV) was confirmed through infrared spectroscopic analysis.

Into a 1 liter reactor equipped like the one described above, 400 cm³ of ortho-dichlorobenzene, 53.9 g of intermediate (XXV) and 14.5 g of hexamethylenediamine were charged.

It was heated to 100° C. and this temperature was maintained for 2 hours. 10 g of sodium hydrate were then added and the temperature was raised to 140° C. The mass was kept at 140° C. for 16 hours, whereafter it was cooled to room temperature and the resulting product was filtered and repeatedly washed with water.

After drying, 62.3 g of product:

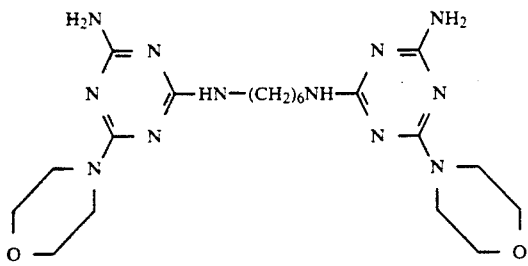

were obtained in the form of a white crystalline powder having m.p.=267°-269° C.

EXAMPLE 4

Into the same 1 liter reactor as used in Example 3, 400 cm³ of xylene, 53.9 g of intermediate (XXV) and 10.8 g of paraphenylenediamine were charged.

Operating according to the same modalities described in said example, there were obtained, after drying, 55.7 g of product:

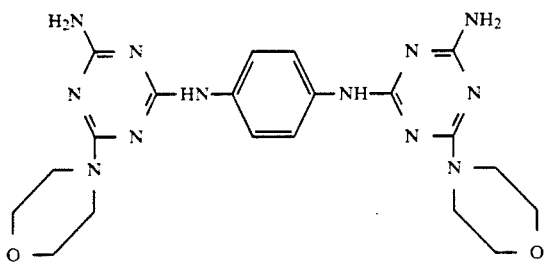

in the form of a white crystalline powder having m.p. greater than 300° C.

EXAMPLE 5

Into a 2 liter reactor, equipped like the one used in the preceding tests, 129 g of cyanuric acid chloride and 1,000 cm³ of methylene chloride were charged.

While cooling from the outside, 40 g of 3-amino-1-propene dissolved in 150 g of water were added, in 90 minutes, to the solution maintained at 0°-2° C.

Maintaining the temperature at 0°-2° C., 28 g of sodium hydrate in 100 g of water were added in 2 hours. The whole was stirred for 2 hours at a temperature of 3°-5° C., whereafter the aqueous phase was separated.

By distillation of methylene chloride, 137 g of intermediate (XXVI):

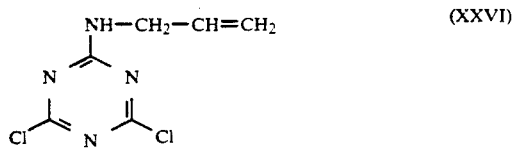

in the form of a white crystalline powder, having m.p.=70°-72° C. and a chlorine content of 34.52% (theoretical value: 34.63%), were obtained.

Into the same apparatus described hereinbefore, 200 g of an ammonia solution at 30% by weight and 500 g of water were charged.

It was heated to 40° C. and then, in 30 minutes and maintaining the temperature at 40° C., 123 g of intermediate (XXVI) were added.

The temperature was brought to 45° C. and was maintained at such value for about 6 hours.

On conclusion, the whole was cooled to room temperature and the obtained product was filtered. The product was then washed with water and dried.

Obtained were 104 g of intermediate (XXVII)

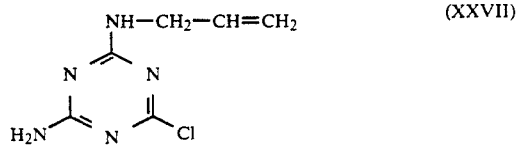

as a white crystalline powder having m.p.=168°-170° C. and a chlorine content of 19.03% (theoretical value: 19.14%).

The structure of intermediates (XXVI) and (XXVII) was confirmed through NMR analysis.

Into a 1.0 liter reactor equipped as described above, there were charged 450 cm³ of xylene, 55.7 g of intermediate (XXVII) and 17.1 g of 2,5-dimethylpiperazine.

The mass was heated to 100° C. for 2 hours, then 12 g of solid sodium hydrate were added and the whole was brought to boiling.

It was maintained at reflux for 18 hours, then it was operated as in the preceding examples.

There were obtained 56.3 g of product:

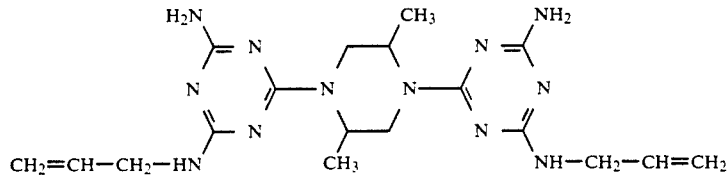

in the form of a white crystalline powder having m.p.=192°-194° C.

EXAMPLE 6

Into a 2 liter reactor equipped as in Example 3, 92.2 g of cyanuric acid chloride, 500 cm³ of acetone and 300 g of ethylenediamine dissolved in 100 g of water were charged.

Maintaining the temperature at 3°-5° C., 15 g of ethylenediamine dissolved in 100 g of water were added in 2 hours. The whole was kept under stirring at 5° C. for 1 hour, then 42 g of solid sodium bicarbonate were added in 1 hour and maintaining the temperature at 5°-7° C. The reaction mass was maintained for 2 hours at 8°-10° C. and then it was heated to 35° C.

At this new temperature and in a 1 hour time, a solution consisting of 30.6 g of 2-hydroxyethylamine in 100 g of water was added.

The temperature was further raised to 40°-45° C., and in 2 hours 20 g of sodium hydrate in 100 g of water were added. The whole was maintained for 1 hour at 50° C., then acetone distillation was started by causing the temperature to rise up to 80° C.

After addition of 81 g of thiomorpholine, it was heated up to the boiling temperature. After 2 hours, 16 g of sodium hydrate in 40 g of water were poured and it was maintained at reflux for further 6 hours.

After cooling to room temperature, the resulting product was filtered and repeatedly washed with water.

After drying, 96.5 g of product:

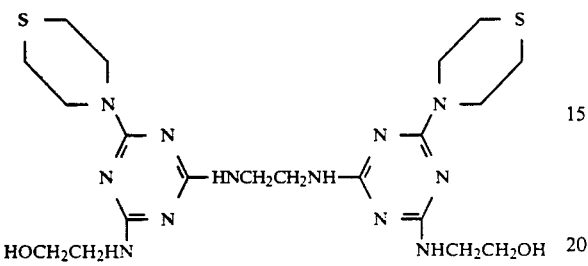

in the form of a white crystalline powder having m.p. greater than 300° C. were obtained.

EXAMPLE 7

Into a 1 liter reactor equipped as described in Example 6, 92.2 g of cyanuric acid chloride and 300 cm³ of acetone were charged.

While cooling from the outside at a temperature of 0°-5° C., 21.3 g of piperazine dissolved in 200 cm³ of acetone were added in 1 hour.

Always at a temperature of 0°-5° C., 20 g of sodium hydrate in 100 g of water were added.

The whole was stirred at 5° C. for further 4 hours, then 200 g of cold water were added; the resulting precipitate was filtered and it was washed with water on the filter.

After drying, 88.7 g of intermediate (XXVIII):

(XXVIII)

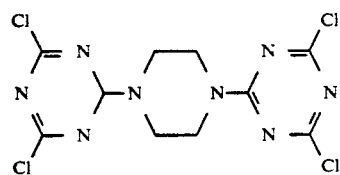

in the form of a white crystalline powder having m.p. greater than 300° C. and a chlorine content equal to 37.4% (theoretical: 37.2%) were obtained.

Into the same 1 liter reactor, but equipped with a heating bath, 400 cm³ of xylene and 76.4 g of intermediate (XXVIII) were charged.

It was heated to a temperature of 80° C. and then, in a 4 hour time, 69.6 g of morpholine and subsequently 32 g of sodium hydrate in 50 g of water were added.

The temperature was gradually raised by eliminating the water through azeotropic distillation, until reaching the boiling temperature of the solvent.

It was maintained at reflux for 8 hours, then it was cooled to room temperature and it was filtered, while abundantly washing with water.

After drying, 98.7 g of product:

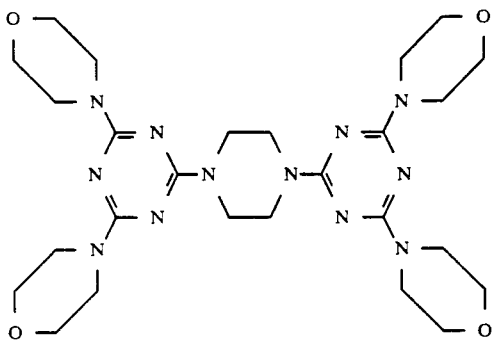

in the form of a white crystalline powder having m.p. greater than 300° C. were obtained.

EXAMPLE 8

400 cm³ of xylene, 64.7 g of intermediate (XXV) and 10.3 g of diethylene triamine are charged to a reactor of 1 liter of capacity, equipped as the hereinabove disclosed one.

The reaction mixture is heated to 100° C. and is kept at this temperature for 2 hours. Then 12 g of sodium hydroxide is added, and the reaction mixture is heated to boiling temperature.

The reaction mass is refluxed for 24 hours, then is cooled down to room temperature and the precipitated solid product is filtered off, with the filter cake being washed with plentiful water.

By oven-drying at 100° C., 56.7 g of product:

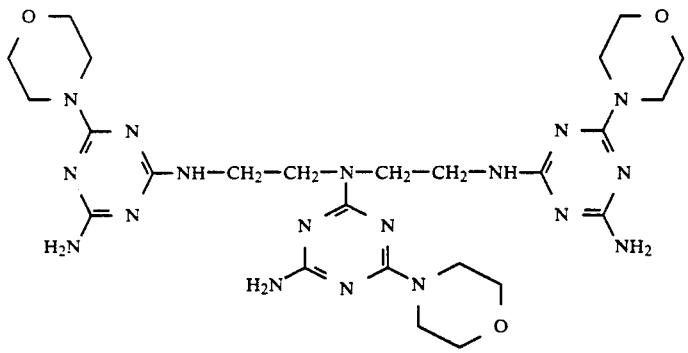

were obtained as a white crystalline powder having m.p. = 207°-208° C.

EXAMPLE 9

500 cm³ of water, 87.3 g of intermediate (XXIII) and 29.2 g of tris(2-aminoethyl)amine are charged to a reactor of 1 liter of capacity, equipped as the hereinabove disclosed one.

The reaction mixture is heated to 50° C. and is kept at this temperature for 2 hours.

Then 24.0 g of sodium hydroxide dissolved in 50 cm³ of water is added over a three hours time, and the reaction mixture is simultaneously heated to boiling temperature.

The reaction mass is refluxed for about 10 hours, then is cooled down to room temperature and the precipitated solid product is filtered off.

The filter cake is washed on the same filter with water, and is oven-dried at 100° C.

89 4 g of product:

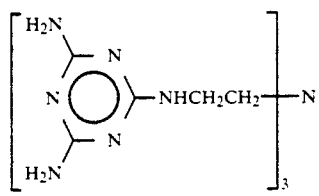

were obtained in the form of a white crystalline powder having m.p.=125°-130° C.

EXAMPLE 10

184.5 g of cyanuric chloride and 1300 cm³ of methylene chloride are charged to a reactor of 3 liters of capacity, equipped in the same way as Example 1.

With the reaction mixture being cooled from the outside, 75 g of 2-methoxyethylamine and 40 g of sodium hydroxide dissolved in 150 cm³ of water are simultaneously added to the reaction mixture, within a 3 hours time, with the pH value of said reaction mixture being kept comprised within the range of from 5 to 7, and the temperature being kept comprised within the range of from 0° to 3° C.

The temperature is maintained comprised within the range of from 0° to 3° C. for a further 3 hours, and the aqueous phase is then separated.

The organic solution is treated with two portions, of 200 cm³ each, of water, with the aqueous phase being separated each time.

By distilling off methylene chloride, 217.5 g of intermediate (XXIX)

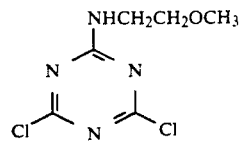

were obtained as a white crystalline powder having m.p.=73°-75° C. and a chlorine content of 31.68% (theoretical value: 31.84%).

To a reactor of 1 liter of capacity, equipped with a stirrer, a thermometer, a charging funnel, a reflux condenser and a heating bath, 400 cm³ of acetone and 133.8 g of intermediate (XXIX) are charged.

The reaction mixture is heated with stirring up to 40° C. until a solution is obtained, then, with the reaction temperature being still kept at 40° C., 102 g of an aqueous solution of ammonia at 30% by weight is added within a 30-minutes time.

The reaction mixture is subsequently heated to 45° C. and is maintained 4 hours at this temperature.

After cooling to 10° C., the precipitated solid product is filter off, and the cake is washed with cold water on the same filter.

After oven-drying at 100° C., 114 g of the intermediate product (XXX):

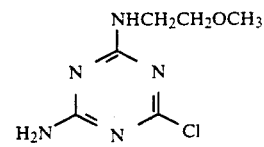

were obtained as a white crystalline powder having m.p.=195°-197° C. and a chlorine content of 17.18% (theoretical value: 17.44%).

The structure of the intermediates (XXIX) and (XXX) was confirmed by I.R. spectroscopic analysis.

500 cm³ of ortho-dichlorobenzene, 91.6 g of intermediate (XXX) and 21.9 g of tris(2-aminoethyl)amine are charged to a reactor of 1 liter of capacity, equipped in the same way as the above disclosed reactor.

The reaction mixture is heated to 100° C. and is maintained at that temperature for 2 hours. Then 18 g of sodium hydroxide is added and the temperature is increased up to 140° C. The reaction mass is maintained at 140° C. for 16 hours, then is cooled to room temperature and the precipitated solid product is filtered off. The filtration cake is washed with plentiful water.

After drying the filtration cake, 88.2 g of the product:

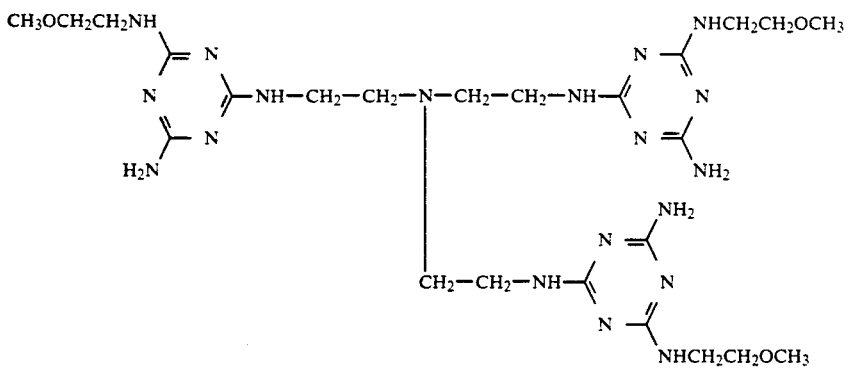

were obtained as a white crystalline powder having m.p. = 190°-195° C.

EXAMPLE 11

500 cm³ of xylene, 86.2 g of intermediate (XXV) and 15.1 g of tetraethylenepentamine are charged to the same reaction equipment of 1 liter of capacity as in Example 10.

The reaction mass is heated up to 80° C. and is maintained at that temperature for 2 hours. 16 g of sodium hydroxide is then added and the temperature is increased up to 110° C.

The reaction mass in maintained at 100° C. for 18 hours, then is cooled down to room temperature and the precipitated solid product is filtered off and the filtration cake is washed with plentiful water.

After oven-drying the cake at 100° C., 82.6 g of the product:

The reaction mixture is stirred at 5° C. for a further 4-hours time, then 200 g of cold water is added, the precipitated solid product is filtered off and the filtration cake is washed with water on the same filter.

After drying, 45.6 g of the intermediate (XXXI):

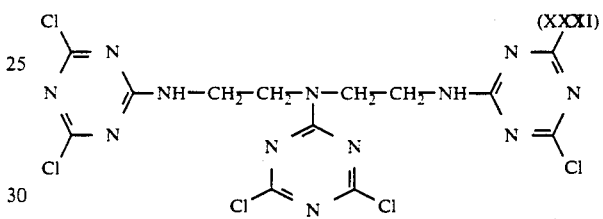

were obtained as a crystalline white powder with m.p. greater than 300° C. and a chlorine content of 38.46% (theoretical value: 38.94%).

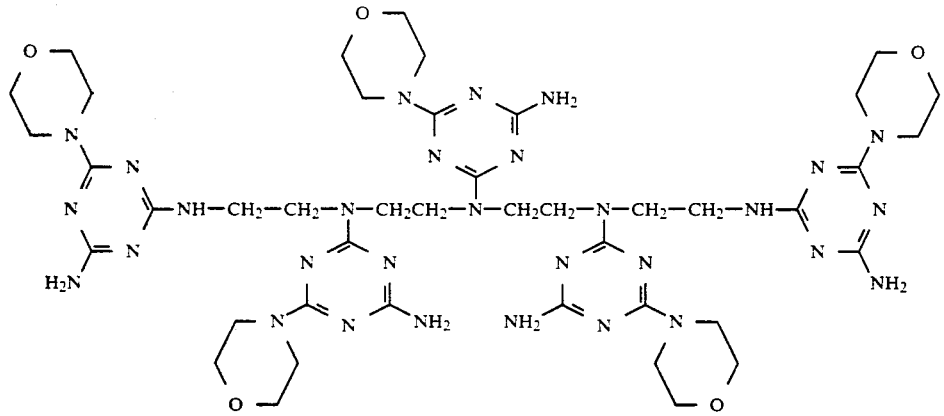

were obtained as a white crystalline powder with m.p. = 178°-183° C.

EXAMPLE 12

55.3 g of cyanuric chloride and 300 cm³ of acetone are charged to a reactor of 1 liter of capacity equipped in the same way as Example 1.

With the reaction mixture being kept cooled at a temperature of 0°-5° C. from the outside, 10.3 g of diethylenetriamine dissolved in 200 cm³ of acetone is added within a 1 hour time.

With the reaction temperature being still kept comprised within the range of from 0° to 5° C., 12 g of sodium hydroxide dissolved in 100 g of water is added.

To the same reactor of 1 liter of capacity, this time equipped with a heating bath, 500 cm³ of xylene and 32.8 g of intermediate (XXXI) are charged.

The reaction mixture is heated to the temperature of 80° C. and subsequently 31.3 g of morpholine and then 14.4 g of sodium hydroxide in 50 g of water are added within a 4-hours time.

The temperature is gradually increased with water being removed by azeotropic distillation, until the solvent boiling temperature is reached.

The reaction mixture is kept 8 hours under refluxing conditions, then is cooled down to room temperature and is filtered. The filtration cake is thoroughly washed with water.

After drying, 43.1 g of product:

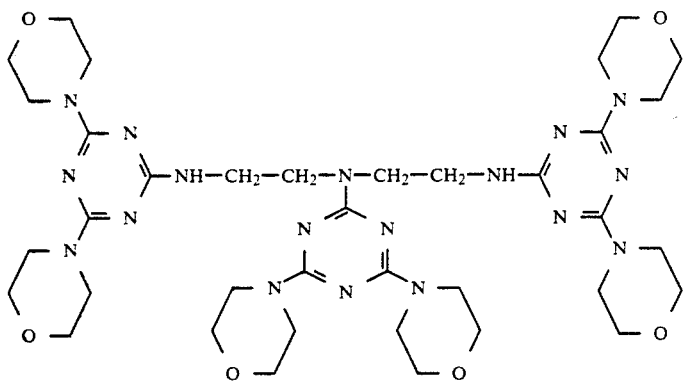

were obtained as a white crystalline powder having m.p.=277°–280° C.

EXAMPLE 13

450 cm³ of water, 91.6 g of intermediate (XXX) and, with stirring, 15.4 g of diethylenetriamine are charged to the same reactor of 1 liter of capacity as of Example 10.

The reaction mass is heated up to 80° C. and is maintained at that temperature for 3 hours.

18 g of sodium hydroxide dissolved in 30 cm³ of water is then added and the temperature of the reaction mixture is increased up to boiling point. The reaction mass is refluxed for 16 hours, then is cooled down to about 10° C. and the precipitated solid product is filtered off and the filtration cake is washed with cold water.

By oven-drying the cake at 100° C., 77.9 g of the product:

The reaction mass is heated up to 80° C. and is maintained at that temperature for 2 hours, then 16 g of sodium hydroxide dissolved in 30 cm³ of water is added.

The temperature of the reaction mixture is increased up to boiling point and the reaction mass is refluxed for 14 hours.

Then by operating in the same way as disclosed in preceding Example 13, 86.2 g of the product:

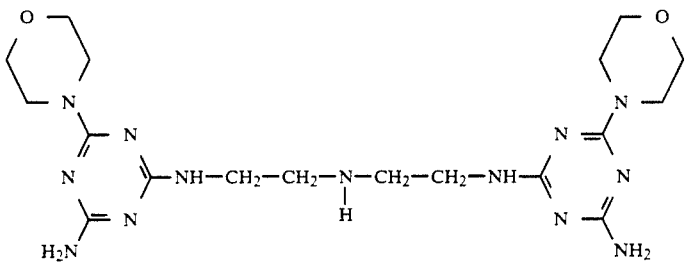

were obtained as a white crystalline powder with m.p.=198°–201° C.

EXAMPLES 15–55

By operating under conditions analogous to those as disclosed in Examples 1 to 14, the compounds of general formula (I) reported in Table 1 are synthesized.

$R_4$, when present, is the triazinic ring having formula:

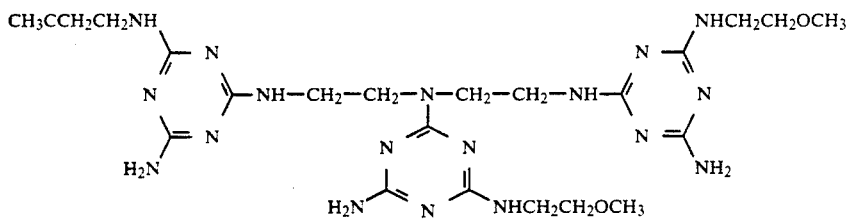

were obtained a white crystalline powder with m.p.=296°–299° C.

EXAMPLE 14

400 cm³ of water, 86.2 g of intermediate (XXV) and, with stirring, 20.6 g of diethylenetriamine are charged to the same reactor of 1 liter of capacity as of preceding Example 13.

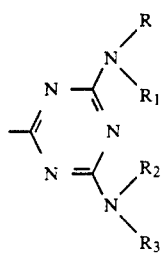

TABLE 1

| EX. No. | R—N—R₁ | | R₂—N—R₃ | | $-Z-\left[-N-Z_1\atop[Z_2]_{la}\right]_b$ | M.P. (°C.) |
|---|---|---|---|---|---|---|
| 15 | morpholino | H | H | H | piperazine (N-...-N-) | 276–278 |
| 16 | CH₂CH₂OCH₃ | H | H | H | piperazine (N-...-N-) | 212–215 |
| 17 | morpholino | H | H | H | —NCH₂CH₂NH—<br>CH₂CH₂OH | 167–170 |
| 18 | H | H | H | H | —HNCH₂CH₂NH— | >300 |
| 19 | H | H | H | H | —HN—(CH₂)₆NH— | 273–276 |
| 20 | (CH₂)₃OC₂H₅ | H | H | H | —HN—⟨C₆H₄⟩—CONH—⟨C₆H₄⟩—NH— | 226–229 |
| 21 | piperidino | H | H | H | piperazine (N-...-N-) | 272–274 |
| 22 | morpholino | H | H | H | —HNCH₂—⟨C₆H₄⟩—CH₂NH— | 240–241 |
| 23 | CH₂CH₂OH | H | H | H | piperazine (N-...-N-) | 252–254 |

TABLE 1-continued

| EX. No. | R—N—R$_1$ | | R$_2$—N—R$_3$ | | $-Z\left[\begin{array}{c}N-Z_1\\|\\{[Z_2]_a}\end{array}\right]_b$ | M.P. (°C.) |
|---|---|---|---|---|---|---|
| 24 | CH$_2$CH$_2$OH | H | CH$_2$CH$_2$OH | H | piperazinyl (–N(CH$_2$CH$_2$)$_2$N–) | 236–240 |
| 25 | H | (CH$_2$)$_5$OH | H | H | —HNCH$_2$CH$_2$NH— | 231–234 |
| 26 | H | H | H | CH$_2$CH$_2$OH | piperazinyl | 260–262 |
| 27 | H | (CH$_2$)$_3$N(CH$_2$H$_5$)$_2$ | H | H | piperazinyl | 281–284 |
| 28 | (CH$_2$)$_3$OH | H | H | H | —NCH$_2$CH$_2$N—, CH$_3$, CH$_3$ | 224–227 |
| 29 | H | morpholinyl | H | H | —NHCH—CH=CH—CHNH—, CH$_3$, CH$_3$ | 227–229 |
| 30 | (CH$_2$)$_3$OCH$_3$ | H | CH$_2$CH$_2$OCH$_3$ | H | —NH—(CH$_2$)$_6$N—, C$_6$H$_{12}$ | 161–163 |
| 31 | CH$_2$CH$_2$OCH$_3$ | H | H | H | —NH—⟨C$_6$H$_4$⟩—NH— | 170–172 |
| 32 | | morpholinyl | | morpholinyl | —NCH$_2$CH$_2$N—, CH$_2$CH$_2$OH, CH$_2$CH$_2$OH | 227–229 |

TABLE 1-continued

| EX. No. | R—N—R₁ | | R₂—N—R₃ | | $-Z-\left[\underset{[Z_2]_a}{N-Z_1}\right]_b-$ | M.P. (°C) |
|---|---|---|---|---|---|---|
| 33 | morpholine (N-O ring) | H | H | H | —HN(CH₂)₂O—(CH₂)₂NH— | 237–240 |
| 34 | thiomorpholine (N-S ring) | H | H | H | trans-1,4-cyclohexane-bis(NHCH₂—/—CH₂NH—) | 142–145 |
| 35 | (CH₂)₂O(CH₂)₂OH | H | H | H | piperazine (N—/—N) | 202–205 |
| 36 | CH₂CH₂OH | CH₃ | H | H | —NHCH₂CH₂NH— | 230–233 |
| 37 | piperazine NH | H | H | H | —NH—(CH₂)₆NH— | 282–284 |
| 38 | N-methylpiperazine (N—CH₃) | H | H | H | piperazine (N—/—N) | 278–281 |
| 39 | morpholine (N-O ring) | H | t-C₈H₁₇ | H | piperazine (N—/—N) | 187–189 |
| 40 | (CH₂)₂OCH=CH₂ | H | H | H | piperazine (N—/—N) | 216–219 |

TABLE 1-continued

| EX. No. | R—N—R$_1$ | | R$_2$—N—R$_3$ | | $-Z-\left[\begin{array}{c}N-Z_1\\ [Z_2]_a\end{array}\right]_b-$ | M.P. (°C.) |
|---|---|---|---|---|---|---|
| 41 | n-C$_4$H$_9$ | H | H | H | —N(piperazine)N— | 174–175 |
| 42 | CH$_2$CH$_2$OCH$_3$ | CH$_2$CH$_2$OCH$_3$ | H | H | —NH—(CH$_2$)$_3$NH— | 149–152 |
| 43 | CH$_2$CH$_2$OH | H | H | H | —HN—C(CH$_3$)$_2$—(cyclohexyl)—C(CH$_3$)$_2$(NH$_2$)—NH— | 215–218 |
| 44 | morpholino | | H | H | —HN—(CH$_2$CH$_2$O)$_2$CH$_2$CH$_2$NH— | 172–175 |
| 45 | morpholino | | H | H | —HNCH$_2$CH$_2$NH— | 265–268 |
| 46 | (CH$_2$)$_3$OH | H | H | H | —N(C$_2$H$_5$)—CH$_2$—CH=CH—CH$_2$—N(C$_2$H$_5$)— | 212–214 |
| 47 | CH$_2$CH$_2$N(morpholino) | H | H | H | —N(piperazine)N— | 274–277 |
| 48 | morpholino | | H | H | —HN(CH$_2$)$_3$N(piperidine)N(CH$_2$)$_3$NH— | 220–222 |
| 49 | CH$_2$CH$_2$OCH$_3$ | H | morpholino | H | —NH—(CH$_2$)$_3$—N—(CH$_2$)$_3$—NH— | 242–246 |

TABLE 1-continued

| EX. No. | R—N—R$_1$ | R$_2$—N—R$_3$ | $-Z-\left[\underset{[Z_2]_a}{N-Z_1}\right]_b$ | M.P. (°C.) |
|---|---|---|---|---|
| 50 | piperidine (N-linked) | H, H | —NH—(CH$_2$)$_2$—N—(CH$_2$)$_2$—NH— | 259–262 |
| 51 | morpholine (N-linked) | n-C$_4$H$_9$, H | —NH—(CH$_2$)$_2$—N—(CH$_2$)$_2$—NH— | 135–142 |
| 52 | H, CH$_2$CH$_2$CH$_2$N(morpholine) | H, H | N—(CH$_2$CH$_2$NH—)$_3$ | 172–177 |
| 53 | morpholine (N-linked) | CH$_2$—CH=CH$_2$, H | —NH—(CH$_2$)$_4$—N—(CH$_2$)$_3$—NH— | 157–161 |
| 54 | CH$_2$CH$_2$OCH=CH$_2$, H | H, H | —NH—(CH$_2$)$_3$—N—(CH$_2$)$_2$—N—(CH$_2$)$_3$—NH— | 199–204 |
| 55 | H, H | H, H | —NH—(CH$_2$)$_2$—N—(CH$_2$)$_2$—NH— | 192–196 |

TABLES 2 AND 3

The tests reported in said tables relate to polymeric compositions containing the products of general formula (I) prepared according to the preceding examples.

Specimens having the shape of small slabs of about 3 mm of thickness were prepared by molding mixtures of granular polymer and additives on a MOORE platen press, with a molding cycle of 7 minutes and a molding pressure of about 40 kg/cm$^2$.

On the so obtained slab specimens, the level of self-extinguishment was determined by measuring the oxygen index (L.O.I. according to ASTM D-2863/77) in a Stanton Redcroft instrument, and applying the "Vertical burning test" which makes it possible for the material to be classified according to three rating levels 94 V-0, 94 V-1 and 94 V-2 according to UL 94 standards (issued by Underwriters Laboratories—U.S.A.).

In Table 2 the values are reported, which were obtained by using an isotactic polypropylene in flakes form having a melt flow index of 12, and an insoluble fraction in boiling n-heptane of 96% by weight.

In Table 3 the values are reported, which were obtained by using low-density polyethylene in granules, with a melt flow index of 7; polystyrene granules containing 5% by weight of butadiene rubber and having a melt flow index of 9; thermoplastic polyurethane granules, either of polyester grade (ESTANE 54600 ® by Goodrich) or of polyether grade (ESTANE 58300 ® by Goodrich), having specific densities repsectively of 1.19 and 1.10 g/cm$^3$; an ethylene-propylene elastomeric copolymer containing 45% by weight of propylene; an acrylonitrile-butadiene-styrene terpolymer having a specific gravity of 1.06 g/cm$^3$, a melt flow index of 1.6 and containing about 40% of acrylonitrile and 20% of butadiene.

TABLE 2

| EXAMPLE No. | PRODUCT EXAMPLE No. | PRODUCT | PP (1) | AO (2) | APP (1) | L.O.I. (ASTM D2863) | UL 94 3 mm |
|---|---|---|---|---|---|---|---|
| 56 | 1 | 8.3 | 70 | 1 | 20.7 | 37.6 | V0 |
| 57 | 2 | 6.0 | 75 | 1 | 18.0 | 34.8 | V0 |
| 58 | 3 | 6.0 | 75 | 1 | 18.0 | 34.6 | V0 |
| 59 | 4 | 5.5 | 76 | 1 | 17.5 | 31.2 | V2 |
| 60 | 5 | 9.0 | 64 | 1 | 26.0 | 41.2 | V0 |
| 61 | 6 | 6.0 | 78 | 1 | 15.0 | 31.8 | V0 |
| 62 | 7 | 6.0 | 75 | 1 | 18.0 | 36.3 | V2 |
| 63 | 8 | 6.0 | 81 | 1 | 12.0 | 31.8 | V1 |
| 64 | 8 | 11.3 | 65 | 1 | 22.7 | 45.3 | V0 |
| 65 | 9 | 9.0 | 72 | 1 | 18.0 | 32.2 | V0 |
| 66 | 10 | 8.3 | 70 | 1 | 20.7 | 36.7 | V0 |
| 67 | 11 | 7.0 | 71 | 1 | 21.0 | 37.4 | V0 |
| 68 | 12 | 6.0 | 75 | 1 | 18.0 | 35.4 | V0 |
| 69 | 13 | 8.3 | 74 | 1 | 16.7 | 34.7 | V0 |
| 70 | 14 | 6.8 | 75 | 1 | 17.2 | 32.8 | V0 |
| 71 | 15 | 10.0 | 64 | 1 | 25.0 | 44.5 | V0 |
| 72 | 16 | 5.0 | 75 | 1 | 19.0 | 35.2 | V0 |
| 73 | 17 | 8.0 | 71 | 1 | 20.0 | 36.1 | V0 |
| 74 | 18 | 5.0 | 74 | 1 | 20.0 | 31.7 | V0 |
| 75 | 19 | 5.0 | 77 | 1 | 17.0 | 28.8 | V1 |
| 76 | 20 | 6.0 | 75 | 1 | 18.0 | 30.9 | V0 |
| 77 | 21 | 7.5 | 76 | 1 | 15.5 | 31.7 | V1 |
| 78 | 22 | 8.0 | 71 | 1 | 20.0 | 30.4 | V0 |
| 79 | 23 | 7.0 | 78 | 1 | 14.0 | 33.1 | V0 |
| 80 | 24 | 7.5 | 77 | 1 | 14.5 | 34.5 | V0 |
| 81 | 25 | 6.0 | 75 | 1 | 18.0 | 32.4 | V0 |
| 82 | 26 | 7.0 | 75 | 1 | 17.0 | 36.2 | V0 |
| 83 | 27 | 9.0 | 72 | 1 | 18.0 | 31.2 | V0 |
| 84 | 28 | 6.2 | 75 | 1 | 17.8 | 31.7 | V0 |
| 85 | 29 | 7.0 | 71 | 1 | 21.0 | 32.4 | V0 |
| 86 | 30 | 8.0 | 73 | 1 | 18.0 | 30.2 | V1 |
| 87 | 31 | 6.5 | 73 | 1 | 19.5 | 30.7 | V1 |
| 88 | 32 | 8.5 | 73 | 1 | 17.5 | 32.9 | V1 |
| 89 | 33 | 7.0 | 71 | 1 | 21.0 | 31.6 | V0 |
| 90 | 34 | 7.0 | 71 | 1 | 21.0 | 33.8 | V0 |
| 91 | 35 | 8.0 | 75 | 1 | 16.0 | 32.9 | V0 |
| 92 | 36 | 7.0 | 71 | 1 | 21.0 | 34.9 | V0 |
| 93 | 37 | 8.3 | 74 | 1 | 16.7 | 32.8 | V0 |
| 94 | 38 | 8.3 | 74 | 1 | 16.7 | 32.5 | V0 |
| 95 | 39 | 6.0 | 75 | 1 | 18.0 | 30.8 | V2 |
| 96 | 40 | 8.0 | 75 | 1 | 16.0 | 32.9 | V0 |
| 97 | 41 | 6.0 | 75 | 1 | 18.0 | 30.3 | V1 |
| 98 | 42 | 6.5 | 73 | 1 | 19.5 | 32.0 | V0 |
| 99 | 43 | 9.0 | 72 | 1 | 18.0 | 34.3 | V0 |
| 100 | 44 | 6.5 | 74 | 1 | 18.5 | 31.2 | V1 |
| 101 | 45 | 6.0 | 75 | 1 | 18.0 | 35.7 | V0 |
| 102 | 46 | 10.0 | 67 | 1 | 22.0 | 37.2 | V0 |
| 103 | 47 | 8.0 | 75 | 1 | 16.0 | 35.1 | V0 |
| 104 | 48 | 6.8 | 75 | 1 | 17.2 | 35.9 | V0 |
| 105 | 49 | 6.8 | 75 | 1 | 17.2 | 35.1 | V0 |
| 106 | 50 | 8.3 | 70 | 1 | 20.7 | 33.2 | V1 |
| 107 | 51 | 7.0 | 71 | 1 | 21.0 | 31.8 | V0 |
| 108 | 52 | 7.4 | 73 | 1 | 18.6 | 32.7 | V0 |
| 109 | 53 | 9.0 | 72 | 1 | 18.0 | 35.6 | V0 |
| 110 | 54 | 8.3 | 74 | 1 | 16.7 | 34.4 | V0 |
| 111 | 55 | 6.5 | 70 | 1 | 22.5 | 34.1 | V0 |
| 112 | 11 | 11.3 | 65 | 1 | *22.7 | 43.5 | V0 |
| 113 | 13 | 6.8 | 75 | 1 | *17.2 | 35.3 | V0 |
| 114 | 15 | 7.5 | 74 | 1 | *17.5 | 36.0 | V0 |
| 115 | 2 | 6.0 | 75 | 1 | 18.0(3) | 32.9 | V0 |
| 116 | 8 | 7.2 | 74 | 1 | 17.8(4) | 32.6 | V0 |

(1) PP = polypropylene
APP = ammonium polyphosphate-Exolit 422 ® (Hoechst)
*APP = ammonium phosphate microencapsulated with melamine formaldehyde resin-Exolit 462 ® (Hoechst).
(2) AO = antioxidant a mixture consisting of 2 parts of dilauryl thiopropionate and 1 part of pentaerythritol tetra [3-(3,5-di-tert.butyl-4-hydroxyphenyl)propionate].
(3) = monoammonium salt from 1-aminoethane-1,1-diphosphonic acid.
(4) = monoammonium salt from 1-hydroxyethane-1,1-diphosphonic acid.

TABLE 3

| EX. No. | POLYMERIC SUPPORT (2) | PRODUCT EXAMPLE No. | POLYMER | PRODUCT | AO (3) | APP (1) | L.O.I. (ASTM-D2863) | UL94 3 mm |
|---|---|---|---|---|---|---|---|---|
| 117 | LDPE | 2 | 69 | 7.5 | 1 | 2.5 | 27.2 | V1 |
| 118 | | 7 | 64 | 8.0 | 1 | 27.0 | 34.1 | V0 |
| 119 | | 45 | 69 | 7.5 | 1 | 22.5 | 29.2 | V0 |
| 120 | | 24 | 69 | 8.6 | 1 | 21.4 | 34.8 | V0 |
| 121 | | 15 | 64 | 10.0 | 1 | 25.0 | 32.7 | V0 |
| 122 | | 16 | 67 | 8.0 | 1 | 24.0 | 34.9 | V0 |
| 123 | | 3 | 64 | 10.0 | 1 | 25.0 | 33.8 | V1 |
| 124 | | 26 | 60 | 11.0 | 1 | 28.0 | 43.6 | V0 |
| 125 | | 23 | 71 | 8.0 | 1 | 20.0 | 30.6 | V1 |
| 126 | | 8 | 60 | 10.0 | 1 | 29.0 | 39.0 | V0 |
| 127 | | 10 | 67 | 8.0 | 1 | 24.0 | 34.9 | V0 |
| 128 | | 11 | 70 | 7.4 | 1 | 21.6 | 33.6 | V0 |
| 129 | | 48 | 65 | 9.7 | 1 | 24.3 | 34.7 | V0 |

TABLE 3-continued

| EX. No. | POLYMERIC SUPPORT (2) | PRODUCT EXAMPLE No. | PARTS BY WEIGHT POLYMER | PARTS BY WEIGHT PRODUCT | AO (3) | APP (1) | L.O.I. (ASTM-D2863) | UL94 3 mm |
|---|---|---|---|---|---|---|---|---|
| 130 |  | 53 | 69 | 7.5 | 1 | 22.5 | 32.8 | V0 |
| 131 | HIPS | 24 | 64 | 11.7 | 1 | 23.3 | 31.8 | V0 |
| 132 |  | 15 | 65 | 11.7 | 1 | 23.3 | 32.6 | V1 |
| 133 |  | 16 | 64 | 10.0 | 1 | 25.0 | 31.0 | V0 |
| 134 |  | 26 | 59 | 10.0 | 1 | 30.0 | 38.0 | V0 |
| 135 |  | 23 | 60 | 13.0 | 1 | 26.0 | 31.2 | V0 |
| 136 |  | 8 | 63 | 9.0 | 1 | 27.0 | 31.7 | V0 |
| 137 |  | 10 | 64 | 10.0 | 1 | 25.0 | 32.0 | V0 |
| 138 |  | 48 | 67 | 9.0 | 1 | 23.0 | 30.8 | V1 |
| 139 | PU | 15 | 70 | 8.2 | 1 | 20.8 | 32.4 | V0 |
| 140 | ester | 17 | 70 | 8.0 | 1 | 21.0 | 34.1 | V0 |
| 141 |  | 8 | 70 | 8.0 | 1 | 21.0 | 34.1 | V0 |
| 142 |  | 11 | 70 | 8.2 | 1 | 20.8 | 32.4 | V0 |
| 143 |  | 48 | 67 | 9.0 | 1 | 23.0 | 33.2 | V0 |
| 144 | PU | 3 | 66 | 10.0 | 1 | 23.0 | 30.6 | V0 |
| 145 | (ether) | 8 | 67 | 9.0 | 1 | 23.0 | 30.4 | V0 |
| 146 | PP/PE | 15 | 60 | 11.0 | 1 | 28.0 | 36.8 | V0 |
| 147 |  | 26 | 60 | 10.0 | 1 | 29.0 | 37.2 | V0 |
| 148 |  | 8 | 63 | 9.0 | 1 | 27.0 | 40.1 | V0 |
| 149 |  | 13 | 60 | 11.0 | 1 | 28.0 | 38.7 | V0 |
| 150 |  | 48 | 59 | 20.0 | 1 | 20.0 | 37.0 | V0 |
| 151 | ABS | 15 | 65 | 11.0 | 1 | 23.0 | 30.4 | V0 |
| 152 |  | 24 | 64 | 10.0 | 1 | 25.0 | 32.2 | V0 |
| 153 |  | 48 | 64 | 10.0 | 1 | 25.0 | 31.8 | V0 |

Footnotes to Table 3
(1)APP = ammonium polyphosphate
(2)LDPE = low-density polyethylene
HIPS = polystyrene containing 5% of butadiene rubber
(Ester) PU = polyester polyurethane
(Ether) PU = polyether polyurethane
PP/PE = propylene-ethylene copolymer
ABS = acrylonitrile-butadiene-styrene terpolymer
(3)AO = antioxidant: a mixture consisting of 2 parts of dilauryl thiopropionate and 1 part of pentaerythritol tetra [3.5-di-tertbutyl-4-hydroxyphenyl)propionate]

EXAMPLE NO. 154 (COMPARATIVE EXAMPLE)

By operating according to the same modalities as of Example Nos. 56 to 116, but with 2,4,6-triamino-1,3,5-triazine being used as the nitrogen-containing compound, the hereinunder specified composition is prepared:

Polypropylene: 72 parts by weight
Antioxidant: 1 part by weight
Ammonium polyphosphate: 18 parts by weight
2,4,6-triamino-1,3,5-triazine: 9 parts by weight By using the above said composition, specimens were prepared and were submitted to tests for their self-extinguishing properties, according to the same modalities as hereinabove disclosed.

The following results were obtained:
L.O.I.: 25.2
UL 94 (3 mm): Class B (the specimen burns).

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Polymeric self-extinguishing compositions comprising:
(a) from 89 to 45 parts by weight of a thermoplastic polymer, or of a polymer endowed with elastomeric properties;
(b) from 8 to 30 parts by weight of one or more ammonium or amine phosphate(s) and/or phosphonate(s);
(c) from 3 to 25 parts by weight of one or more compound(s) derivatives of 2,4,6-triamino-1,3,5-triazine, having the formula (I):

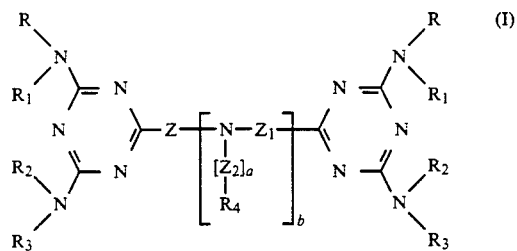

wherein the radicals from R to $R_3$, which can be either equal to or different from one another, and can have different meanings in each triazinic ring are: H; $(C_1-C_{18})$-alkyl; $(C_2-C_8)$-alkenyl; $(C_6-C_{16})$-cycloalkyl or -alkylcycloalkyl, optionally substituted with a hydroxy or $(C_1-C_4)$-hydroxyalkyl function;

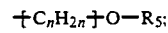

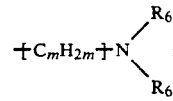

wherein:
n=an integer within the range of from 2 to 8;

m = an integer within the range of from 2 to 6;

$R_5$ = H; ($C_1$-$C_8$)-alkyl; ($C_2$-$C_6$)-alkenyl; $\{C_pH_{2p}\}$—O—$R_7$; wherein p is an integer within the range of from 1 to 4 and $R_7$ is either H or a ($C_1$-$C_4$)-alkyl; ($C_6$-$C_{12}$)-cycloalkyl or -alkylcycloalkyl;

the radicals $R_6$, which can be either equal to, or different from, one another, are:

H; ($C_1$-$C_8$)-alkyl; ($C_2$-$C_6$)-alkenyl; ($C_6$-$C_{12}$)-cycloalkyl or -alkylcycloalkyl; ($C_1$-$C_4$)-hydroxyalkyl; or the moiety:

is replaced by a heterocyclic radical linked to the alkyl chain through the nitrogen atom and possibly containing another heteroatom;

or in formula (I) at least one of the moieties

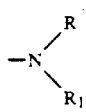

and

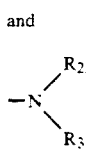

is replaced by a heterocyclic radical linked to the triazinic ring through the nitrogen atom and optionally containing another heteroatom;

a is either 0 or 1;
b is 0 or an integer within the range of from 1 to 5;
$R_4$ is hydrogen or:
$R_4$ is hydrogen or:

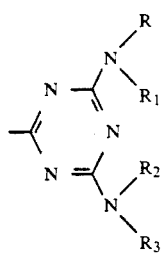

and its meaning can vary inside each repeating unit; when b is zero,

Z is a divalent radical comprised in one of the following formulas:

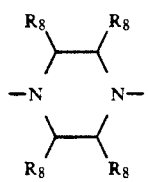
(II)

where radicals $R_8$, like or different from one another, are hydrogen or ($C_1$-$C_4$)-alkyl;

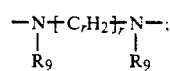
(III)

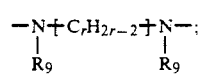
(IV)

where r is an integer comprised within the range of from 2 to 14; $R_9$ is hydrogen; ($C_1$-$C_4$)-alkyl; ($C_2$-$C_6$)-alkenyl; ($C_1$-$C_4$)-hydroxyalkyl;

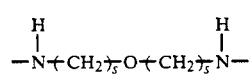
(V)

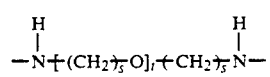
(VI)

where s is an integer within the range of from 2 to 5 and t is an integer within the range of from 1 to 3;

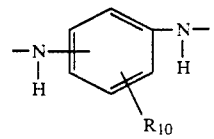
(VII)

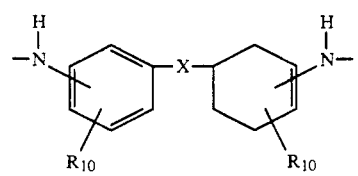
(VIII)

where:
X is a direct bond C—C; O; S; S—S; SO; $SO_2$; NH; $NHSO_2$; NHCO; N=N; $CH_2$;
$R_{10}$ is hydrogen; hydroxyl; ($C_1$-$C_4$)-alkyl; ($C_1$-$C_4$)-alkoxyl;

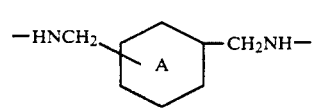
(IX)

where A can be a saturated or unsaturated cycle;

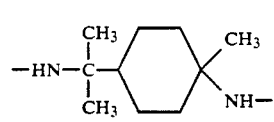
(X)

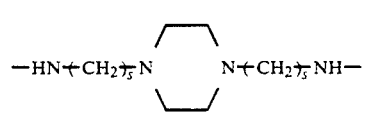
(XI)

where s has the hereinabove defined meaning;
when b is an integer within the range of from 1 to 5, the group:

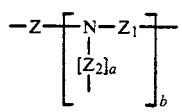

is a polyvalent radical comprised in one of the following formulas:

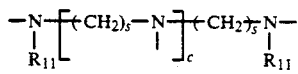   (XII)

where:

$R_{11}$ is either hydrogen or $(C_1-C_4)$-alkyl;

c is an integer within the range of from 1 to 5; the indexes s, which can be either equal to or different from each other, have the hereinabove defined meaning;

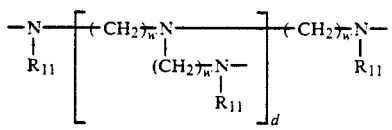   (XIII)

where:

$R_{11}$ has the hereinabove defined meaning;
w is an integer within the range of from 2 to 4;
d is either 1 or 2.

2. Self-extinguishing polymeric compositions according to claim 1, wherein one or both of the following moieties:

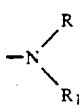

and

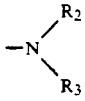

in formula (I) is (are) replaced by heterocyclic radicals selected from:
aziridine; pyrrolidine; piperidine; morpholine; thiomorpholine; piperazine; 4-methylpiperazine; 4-ethylpiperazine; 2-methylpiperazine; 2,5-dimethylpiperazine; 2,3,5,6-tetramethylpiperazine; 2,2,5,5-tetramethylpiperazine; 2-ethylpiperazine; 2,5-diethylpiperazine.

3. Self-extinguishing polymeric compositions according to claim 1, wherein at least one of the radicals from R to $R_3$ in formula (I) is replaced by:

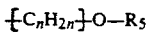

wherein:
n is an integer within the range of from 2 t 4 and $R_5$ is H or $(C_1-C_4)$-alkyl.

4. Self-extinguishing polymeric compositions according to claim 1, wherein at least one of the following moieties:

and

in formula (I) is replaced by an $-NH_2$ radical.

5. Self-extinguishing polymeric compositions according to claim 1, wherein the moiety:

in formula (I) is replaced by a heterocyclic radical selected from among:
aziridine; pyrrolidine; piperidine; morpholine; thiomorpholine; piperazine; 4-methylpiperazine; or 4-ethylpiperazine.

6. Self-extinguishing polymeric compositions according to claim 1, wherein the ammonium phosphate(s) as mentioned under (b) have the formula

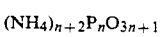

wherein n is an integer equal to, or greater than, 2.

7. Self-extinguishing polymeric compositions according to claim 1, wherein the ammonium phosphate(s) as mentioned under (b) have the formula

wherein n is a numeral within the range of from 50 to 500.

8. Self-extinguishing polymeric compositions according to claim 1, wherein the amine phosphate(s) as mentioned under (b) are selected from among dimethylammonium or diethylammonium phosphate; ethylenediamine phosphate; melamine ortho- or pyrophosphate.

9. Self-extinguishing polymeric compositions according to claim 1, wherein the ammonium phosphate(s) as mentioned under (b) are the mono or polyammonium derivatives from mono or polyphosphonic acids.

10. Self-extinguishing polymeric compositions according to claim 1, wherein the (a) polymer is selected from polymers and copolymers of olefins of formula

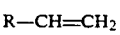

wherein R is a hydrogen atom or a $(C_1-C_8)$-alkyl or -aryl radical; acrylonitrile/butadiene/styrene copolymers (ABS); styrene/acrylonitrile copolymers (SAN); polyurethane; poly(ethylene terephthalate); poly(butylene terephthalate); polyamides.

11. Self-extinguishing polymeric compositions according to claim 10, wherein the olefinic polymers and copolymers are selected from:
(1) either isotactic or prevailingly isotactic polypropylene;
(2) HDPE, LLDPE, LDPE polyethylene;

(3) crystalline copolymers of propylene with minor proportions of ethylene and/or other alpha-olefins, such as 1-butene, 1-hexene, 1-octene, 4-methyl-pentene;

(4) heterophasic compositions comprising (A) a fraction constituted by a propylene homopolymer and one of the copolymers as specified under above item (3); and (B) a copolymeric fraction constituted by elastomeric copolymers of ethylene with an alpha-olefin, optionally containing minor proportions of a diene, wherein the alpha-olefin is preferably selected from propylene and 1-butene;

(5) elastomeric copolymers of ethylene with alpha-olefins optionally containing minor proportions of a diene.

12. Molded articles obtained from the compositions according to claim 1.

* * * * *